United States Patent
Liu et al.

(10) Patent No.: US 8,208,714 B2
(45) Date of Patent: Jun. 26, 2012

(54) FORMATION OF PRESCRIBED PATTERN ON WAFER FOR USE IN SEM DEFECT OFFSET

(75) Inventors: Mu-Chieh Liu, Jhubei (TW); Hsiao Wen Chung, Taipei (TW); Jeng-Huei Yang, Taichung (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 415 days.

(21) Appl. No.: 12/470,269

(22) Filed: May 21, 2009

(65) Prior Publication Data
US 2010/0296722 A1    Nov. 25, 2010

(51) Int. Cl.
*G06K 9/00* (2006.01)
(52) U.S. Cl. ........................................... 382/149
(58) Field of Classification Search ............... 382/149
See application file for complete search history.

(56) References Cited

U.S. PATENT DOCUMENTS

| 6,407,373 | B1 | 6/2002 | Dotan | |
|---|---|---|---|---|
| 2005/0122508 | A1* | 6/2005 | Uto et al. | 356/237.2 |
| 2006/0239536 | A1* | 10/2006 | Shibuya et al. | 382/149 |

OTHER PUBLICATIONS

A. Stamper, et al. "First-Time-Right" Recipe Optimization for Wafer Inspection. Semiconductor.net online magazine article, Apr. 1, 2008. www.semiconductor.net/index. asp?layout=talkbackCommentsFull& . . . USA.

* cited by examiner

*Primary Examiner* — Hwa Lee
(74) *Attorney, Agent, or Firm* — Duane Morris LLP; Steven E. Koffs

(57) ABSTRACT

A prescribed pattern is formed at a plurality of known locations on a semiconductor wafer. The plurality of known locations are incorporated into a defect map that includes a location of at least one defect detected by an in-line inspection of the wafer. The defect map including the plurality of known locations and the location of the at least one defect is transmitted to a scanning electron microscope (SEM). The SEM uses the known locations to calculate a defect offset for use in imaging the at least one defect in the SEM.

20 Claims, 7 Drawing Sheets

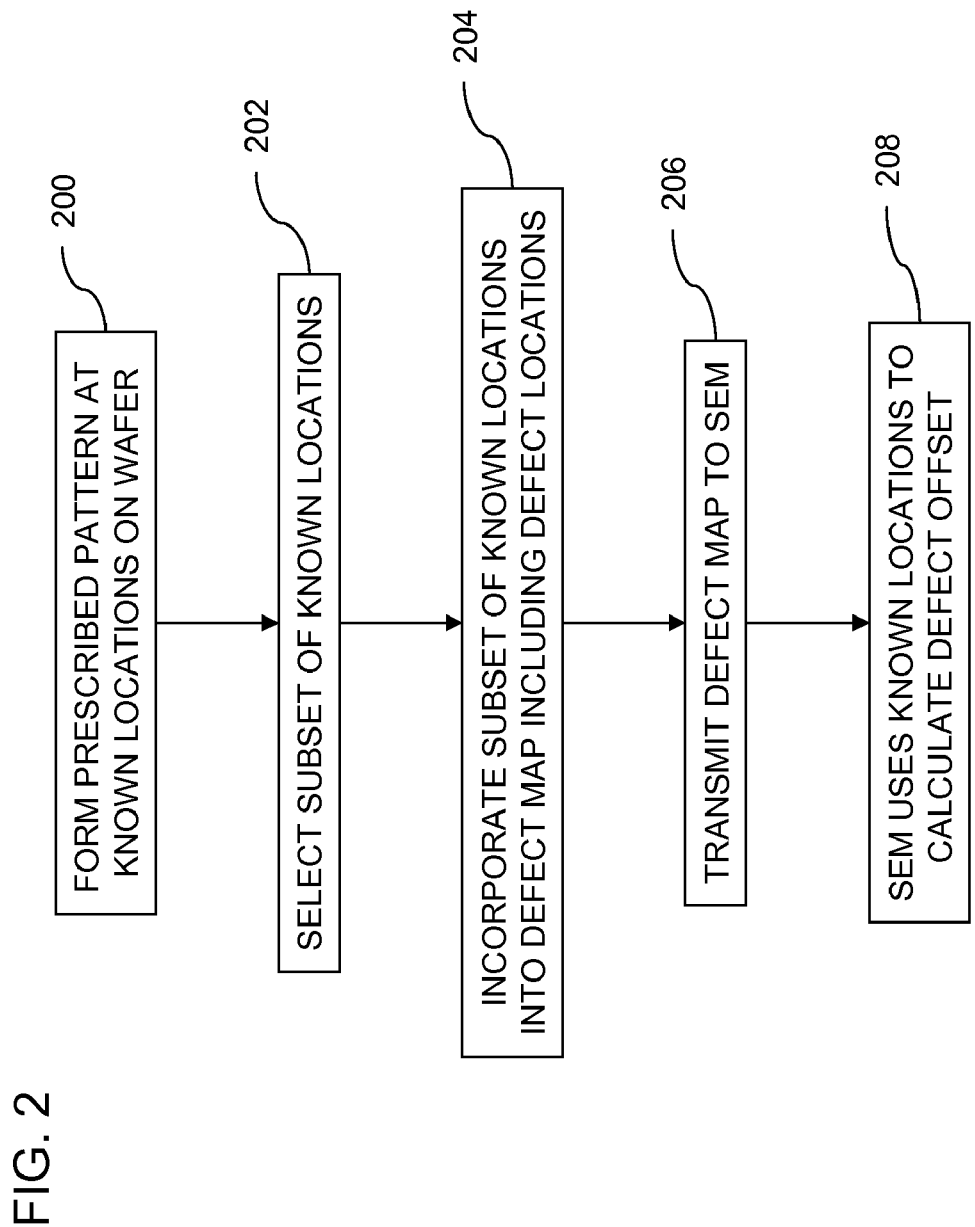

FORMATION OF PRESCRIBED PATTERN ON WAFER FOR USE IN SEM DEFECT OFFSET

TECHNICAL FIELD

The present disclosure relates to defect review systems generally, and more particularly, to defect review systems for semiconductor substrates.

BACKGROUND

Fabrication of semiconductor products involves the formation of microelectronic devices on various layers of a semiconductor substrate. To verify the integrity of the fabrication process, a variety of tests and inspections are performed, including optical tests to detect the presence of defects, such as undesired particles and undesired remnants of material layers that were removed during processing. As the size of the semiconductor devices is reduced, the size of the device features to be measured approaches the limits of measurement tools.

U.S. Pat. No. 6,407,373 (the '373 patent) is expressly incorporated by reference herein. The '373 patent describes a two-part inspection method. An in-line inspection and review is performed to detect defects on the semiconductor wafer during the manufacturing process. Classification of defects on the semiconductor wafer involves, the ability to extract accurate information such as defect size, shape, and boundary in order to identify the sources of the defects. An optical measurement is performed in situ, in the processing tool.

The size of the defects to be detected may be below the resolution of the optical instrument, so optical measurements are not sufficiently accurate for pinpointing the locations of the defect and classifying the defect. On the other hand, a scanning electron microscope (SEM) can resolve features with a size of only a few nanometers, but is too slow to use for inspecting the entire wafer. Thus, a two step approach involves initial inline detection of the approximate location of the defects by in situ optical measurement in the processing tool, and incorporation of the approximate locations of the detected defects into a defect map. The processing tool transmits the defect map containing the locations of the detected defects to the SEM. The SEM uses the defect map to inspect small regions containing the locations identified in the defect map, and "re-detects" the defects. During the "re-detection," the precise location and classification of the defects are determined. By using the defect map, the SEM re-detection takes much less time than would be required for SEM classification without the initial in situ detection. Nevertheless, the duration of the re-detection in the SEM is increased by the presence of systematic errors (rotational and transnational displacements) from the in situ inspection system included in the defect map.

As described in the '373 patent, to eliminate systematic errors of the inspection system from the defect map, a defect offset process is performed by the SEM. The SEM uses the defect map to re-detect a prescribed number of defects (e.g., five defects). The SEM calculates the defect offset, based on the differences between the in situ defect locations in the defect map and the actual locations measured by the SEM. The calculated defect offset is then applied to the remaining points in the defect map to improve the accuracy of the approximate defect locations in the defect map, so that the SEM can re-detect the remaining defects more quickly.

Nevertheless, where the systematic error is relatively large, the amount of time for re-detecting the prescribed number of defects used for defect offset is also large. Further, some types of defects cannot be effectively re-detected by SEM, such as defects buried under (or within) an optically transparent layer.

SUMMARY

In some embodiments, a method comprises forming a prescribed pattern at a plurality of known locations on a semiconductor wafer. The plurality of known locations are incorporated into a defect map that includes a location of at least one defect detected by an in-line inspection of the wafer. The defect map including the plurality of known locations and the location of the at least one defect is transmitted to a scanning electron microscope (SEM). The SEM uses the known locations to calculate a defect offset for use in imaging the at least one defect in the SEM.

In some embodiments, an apparatus comprises a semiconductor processing tool for forming a prescribed pattern at a plurality of known locations on a semiconductor wafer. A processor is provided for incorporating the plurality of known locations into a defect map that includes a location of at least one defect detected by an in-line inspection of the wafer in the tool. The processor is configured for transmitting the defect map including the plurality of known locations and the location of the at least one defect to a scanning electron microscope (SEM). The SEM is configured to use the known locations to calculate a defect offset for use in imaging the at least one defect in the SEM.

In some embodiments, a machine readable storage medium contains program code, such that when the program code is executed by a processor, the processor performs a method comprising controlling a tool to form a prescribed pattern at a plurality of known locations on a semiconductor wafer. The plurality of known locations are incorporated into a defect map that includes a location of at least one defect detected by an in-line inspection of a wafer. The defect map including the plurality of known locations and the location of the at least one defect is transmitted to a scanning electron microscope (SEM). The SEM uses the known locations to calculate a defect offset for use in imaging the at least one defect in the SEM.

BRIEF DESCRIPTION OF THE DRAWINGS

FIG. 2 is a flow chart of a method for providing data for defect offset calculation, in the system of FIG. 1.

DETAILED DESCRIPTION

Figure 1:
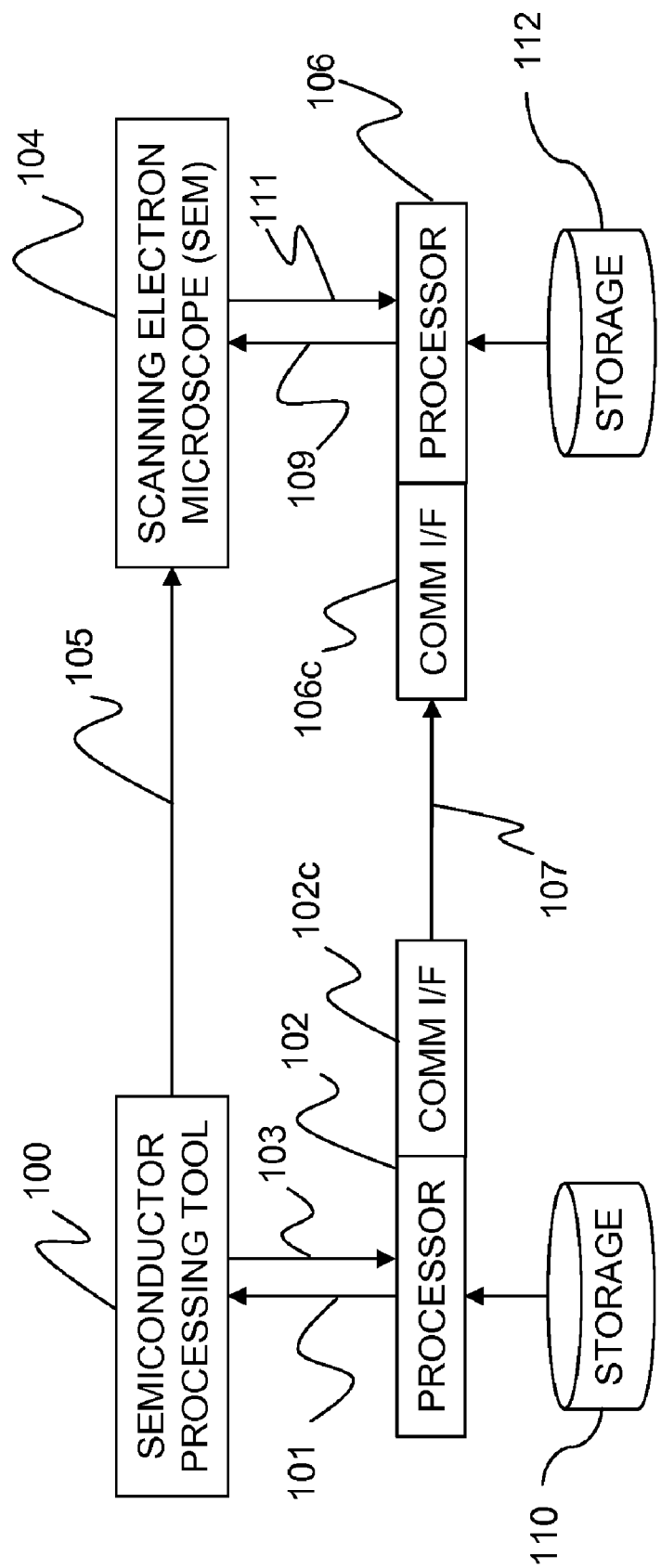
FIG. 1 is a block diagram of an exemplary system, in accordance with an embodiment.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation.

FIG. 1 is a block diagram of an exemplary apparatus for performing at least one semiconductor fabrication processing step, and for detecting and categorizing defects on a semiconductor substrate, such as a silicon wafer with one or more devices and/or material layers formed thereon. A semiconductor processing tool 100 is provided for forming a prescribed pattern at a plurality of known locations on a semiconductor wafer. In some embodiments, the tool has a single processing chamber for performing a deposition or material removal step. In other embodiments, the tool is an integrated tool having a plurality of processing chambers connected by a central buffer chamber, permitting performance of one or more processing steps and a metrology step without removing the wafer from the vacuum environment of the tool.

A processor 102 controls the operation of the semiconductor processing tool 100. The processor 102 transmits control signals 101 to the tool 100 directing tool 100 to form a prescribed pattern on the wafer at a plurality of locations. The processor 102 also receives data 103 from the tool 100, representing locations of one or more defects detected by the optical measurement device (not shown) within the tool 100, during in-line inspection of the wafer in the tool 100. The processor 102 generates a defect map containing the locations of the detected defects, for transmission to the SEM 104. The processor 102 also incorporates the plurality of known locations into the same defect map that includes a location of the defect(s) detected by in-line optical inspection of the wafer in the tool 100.

The processor 102 has a machine readable storage device 110, such as a flash memory, hard disk drive (HDD), compact disk read only memory (CD-ROM) drive, digital versatile disk (DVD)-ROM drive, blue ray disk (BD)-ROM drive or the like. In various embodiments, the storage device 110 may have a fixed medium (e.g., memory or HDD), or a removable medium (e.g., CD-ROM, DVD-ROM, BD-ROM). The storage device 110 may store computer program code for controlling operation of tool 100. The storage device 110 stores and provides pertinent data, such as the configuration of the prescribed pattern, and the locations at which the prescribed pattern is to be formed. The storage device 110 also receives and stores the defect map from the tool 100. In some embodiments, the processor 102 adds a flag to the entries in the defect map corresponding to the instances of the prescribed pattern, so that the processor 106 of SEM 104 can identify and use these entries for the defect offset, in preference to the locations of the actual defects detected during optical inspection.

The processor 102 has a wired or wireless communications interface 102c for transmitting the defect map including the plurality of known locations and the location of the at least one defect to the processor 106 of SEM 104. The communications interface 102c may include TCP/IP, Ethernet, IEEE 1394 ("FIREWIRE™"), IEEE 802.11 (WiFi), and/or other communications protocol.

In some embodiments, the processor 102 is contained within the housing of the tool 100. In other embodiments, the processor 102 is housed separately in a unit in wired or wireless communication with an internal processor (not shown) in the tool 100. The processor 102 may be a microprocessor, a programmable logic controller or a digital signal processor implemented in application specific integrated circuitry (ASIC).

When the inline inspection is completed, the wafer 105 is transported from the tool 100 to the scanning electron microscope (SEM) 104, by an automated materials handling system (AMHS), not shown. The AMHS may include an overhead hoist transport (OHT) that moves the wafer between tool 100 and SEM 104, and may include a stocker and/or overhead hoist buffer (OHB) for temporarily storing the wafer between outputting the wafer from the tool 100 and depositing the wafer 105 at the SEM 104. Also, during this time, the processor 102 controlling the tool 100 delivers the defect map containing the known locations of the prescribed pattern and the locations of the defects found by the inline inspection to the processor 106 for the SEM 104.

The processor 106 of SEM 104 is configured to use the known locations to calculate a defect offset for use in imaging the at least one defect in the SEM. For example, a commercially system available "SEMVision" SEM system from Applied Materials, Inc. of Santa Clara, Calif. is configured with a programmed processor to perform defect offset. The SEM 104 searches for the prescribed pattern at the known locations in the same manner that the SEM searches for the detected defects listed in the defect map. Because the precise locations of the prescribed pattern are known, the SEM can rapidly perform re-detection of the prescribed patterns. Further, because the locations of the prescribed pattern are known, errors due to the limited accuracy of in situ optical measurement are avoided.

In some embodiments, the processor 106 is contained within the housing of the SEM 104. In other embodiments, the processor 106 is housed separate separately in a unit in wired or wireless communication with the SEM 104. The processor 106 may be a microprocessor, a programmable logic controller or a digital signal processor implemented in application specific integrated circuitry (ASIC).

The processor 106 has a machine readable storage device 112, such as a flash memory, HDD, CD-ROM drive, DVD-ROM drive, BD-ROM drive or the like. The storage device 112 may store computer program code for controlling operation of SEM 104, and for performing the defect offset computation. The storage device 112 receives and stores the defect map received from the processor 102 of tool 100. The storage device 112 may also store the calculated defect offset, in the form of a combination of a translation and/or a rotation.

The processor 106 has a wired or wireless communications interface 106c for receiving the defect map that includes the plurality of known locations and the location of the at least one defect from processor 102 of tool 100. The communications interface 106c may include TCP/IP, Ethernet, IEEE 1394 ("FIREWIRE™"), IEEE 802.11 (WiFi), and/or other communications protocol.

FIG. 2 is a flow chart of an exemplary method performed by the apparatus of FIG. 1.

At step 200, the prescribed pattern is formed at a plurality of known locations on the wafer 105. The prescribed pattern may be formed on the wafer 105 by adding the pattern to one of the masks used for an existing process step. The prescribed pattern may be formed in some or all of the dies on the wafer, and/or in some or all of the scribe lines on the wafer. At least two defect (or prescribed pattern) locations are used for defect offset, but preferably at least five or six locations are provided. If the prescribed pattern is formed on fewer than all of the dies, or in fewer than all of the scribe lines, then the instances of the prescribed pattern are preferably spaced apart from each other by distances on the order of magnitude of the wafer radius.

At step 202, the processor 102 associated with the tool 100 selects a subset of the known locations at which the prescribed pattern is formed, for incorporation into the defect map. The subset may include all of the instances of the prescribed pattern or fewer than all of the instances of the prescribed pattern, depending on the number of instances. If the subset includes fewer than all of the instances of the prescribed pattern, then the selected instances of the prescribed pattern are preferably spaced apart from each other by distances on the order of magnitude of the wafer radius.

At step 204, the subset of known locations are incorporated into the defect map that includes a location of at least one defect detected by an in-line inspection of the wafer. The arrangement of the prescribed pattern locations and detected defect locations is optional. In some embodiments, all the locations are sorted by location. In other embodiments, the known locations of the prescribed pattern are all grouped together within the defect map.

At step 206, the processor 102 associated with the tool 100 transmits the defect map including the plurality of known locations and the location of the at least one defect to the processor 106 of the scanning electron microscope (SEM) 104.

At step 208, the processor 106 of SEM 104 uses the known locations to calculate a defect offset for use in imaging the at least one defect in the SEM 104. In some embodiments, the processor 106 selects specific entries from the defect map that are identified as being the prescribed pattern, for use in the defect offset computation. In other embodiments, the processor may use a different criterion for selecting the locations to be used for defect offset. For example, the processor 208 may use the locations of the prescribed pattern if the number of defects detected during inline optical inspection is fewer than the optimal number of locations to be used for defect offset computation. Following the defect offset computation, the SEM 104 can remove the systematic errors from all of the defect map locations, and perform the redetection of the detected defects in the defect map more quickly.

Figure 3A:
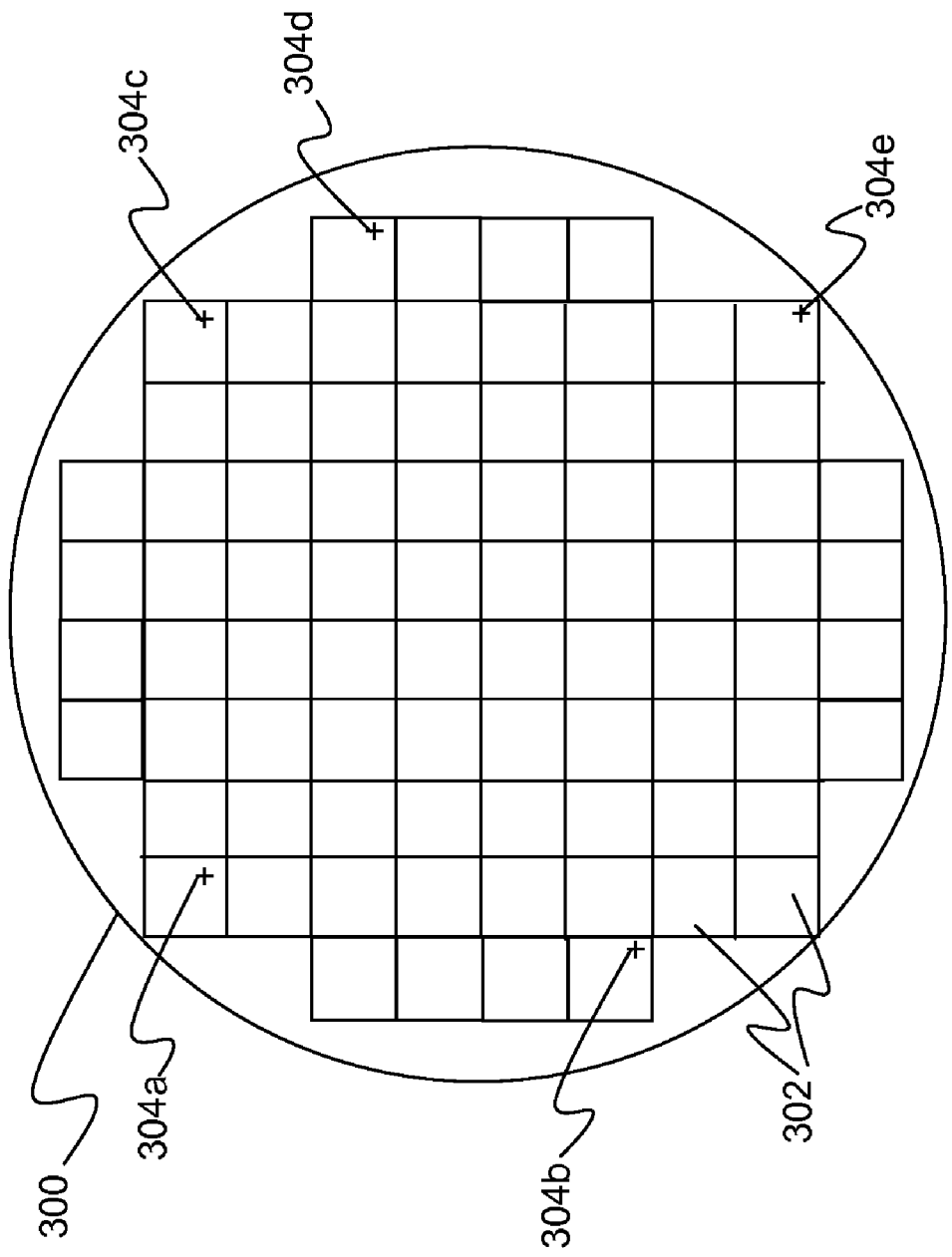
FIGS. 3A and 3B are diagrams of a wafer having a prescribed pattern formed in a plurality of dies, in accordance with an embodiment.

FIG. 3A shows an example of a wafer 300 having a plurality of dies 302. At least some of the dies 302 have instances 304a-304e of a prescribed pattern. In some embodiments, only a small subset of the dies 302 have the prescribed pattern 304a-304e, and the locations of all of the patterns in the subset of dies is included in the defect map.

Figure 3B:
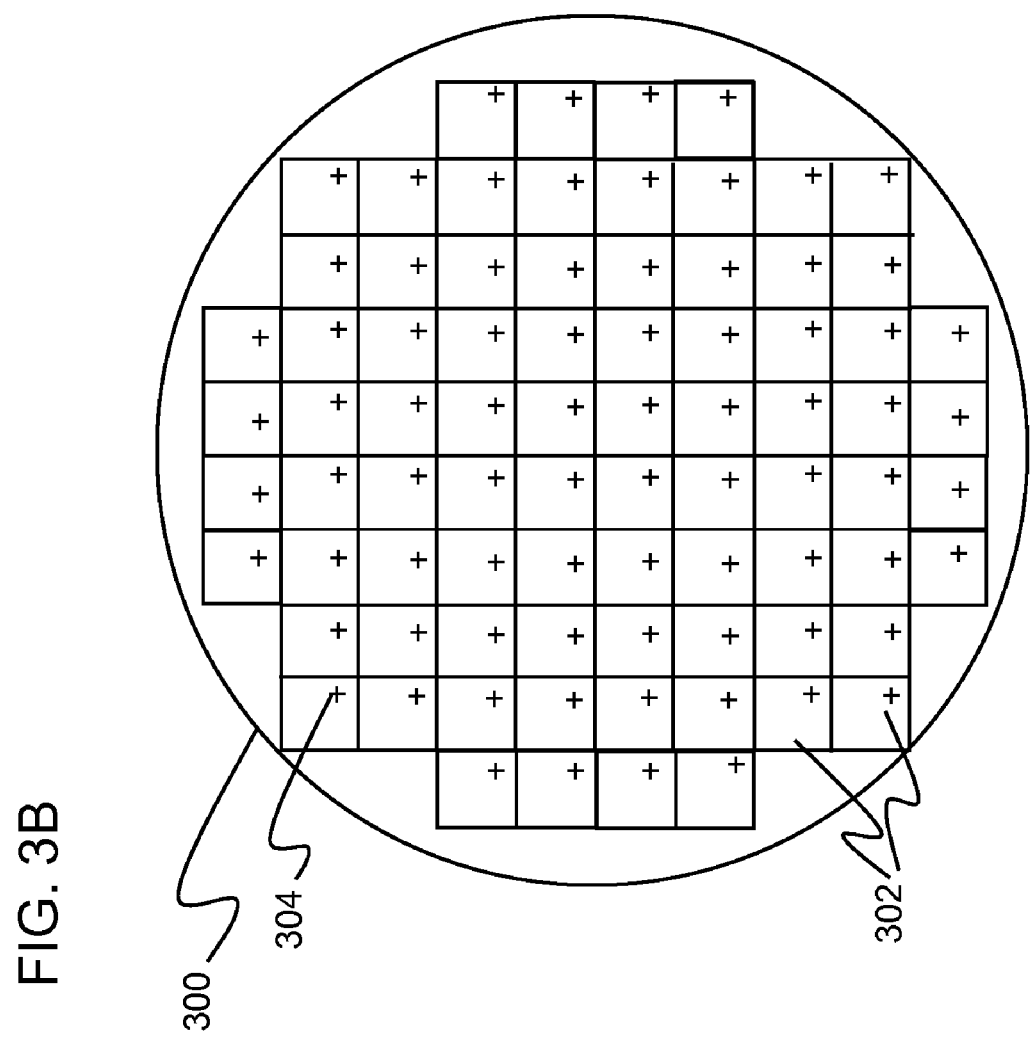

In some embodiments, as shown in FIG. 3B, every die 302 has an instance of the prescribed pattern at the same known, within-die location relative to edges of the die 302. The locations of the prescribed pattern in a small subset (e.g., five or six) of the dies 302 are added to the defect map and subsequently used by the processor 106 of SEM 104 for the defect offset determination. The processor 102 is configured for selecting a subset of the occurrences of the prescribed pattern in a respective subset of the dies 302 for incorporation into the defect map.

In some embodiments, the prescribed pattern is a distinctive pattern that is not used in the circuitry of any of the dies 302. For example, as shown in FIGS. 3A and 3B, the prescribed pattern may be a cross-304a-304d.

In some embodiments, the prescribed pattern is positioned at a portion of the dies 302 that is free of circuit patterns. Preferably, the prescribed pattern is shaped differently from typical particles and metal defects that are found on similar integrated circuits.

Figure 4A:
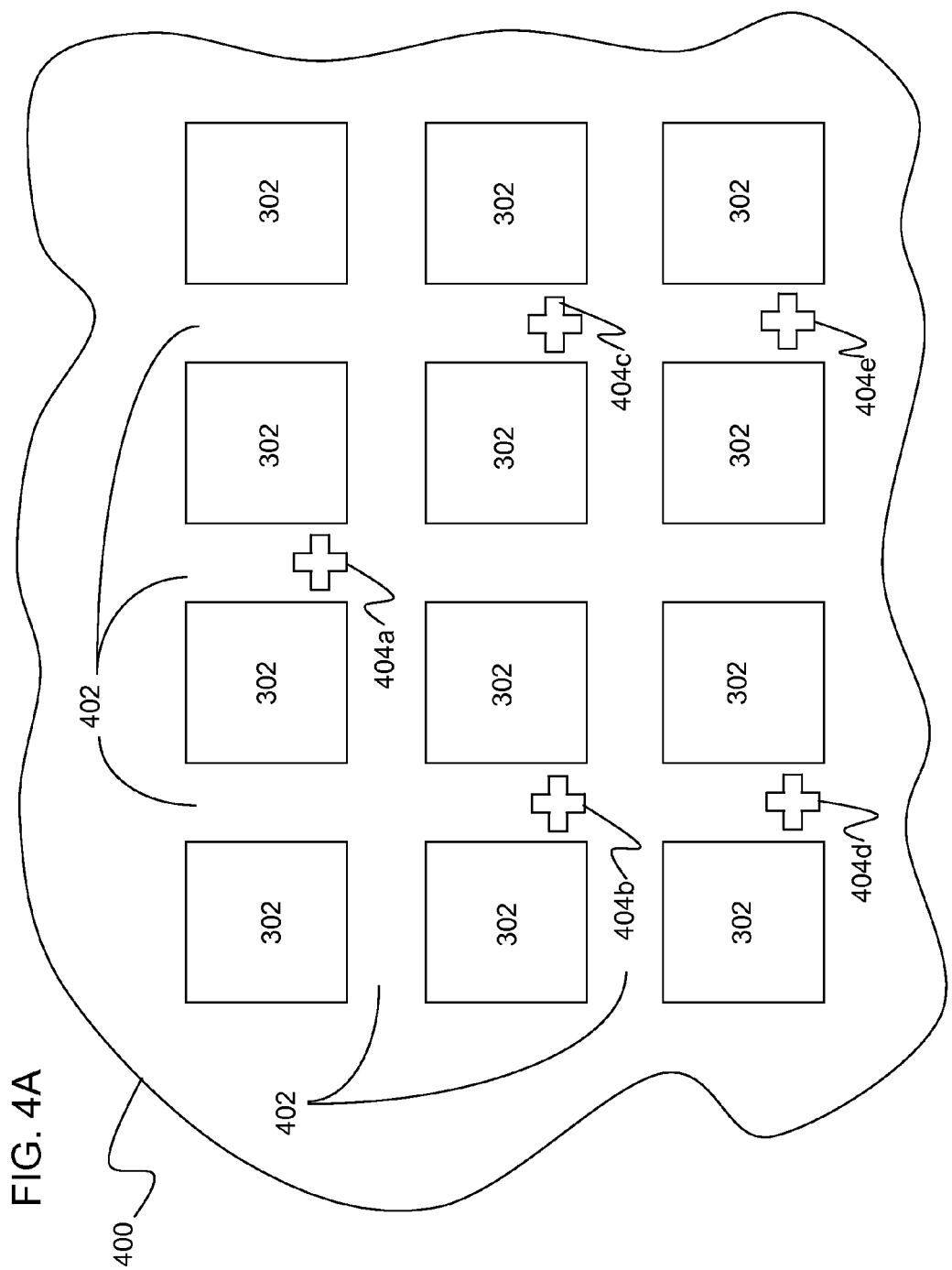
FIGS. 4A and 4B are diagrams of a wafer having a prescribed pattern formed in a plurality of scribe lines, in accordance with an embodiment.

FIG. 4A shows an example in which the wafer 400 has a plurality of scribe lines 402, and some of the scribe lines 402 have instances 404a-404e of a prescribed pattern.

Figure 4B:
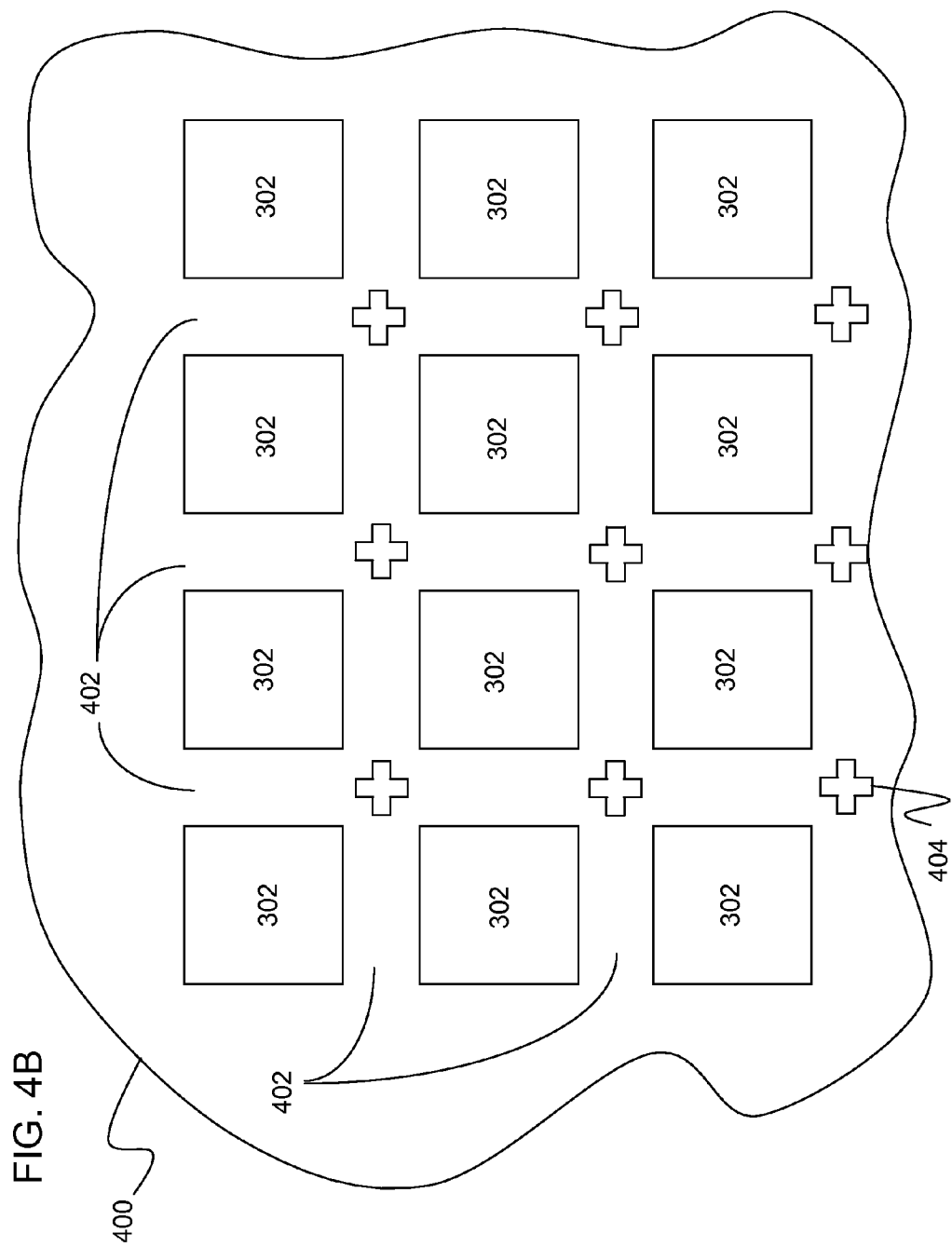

In some embodiments, as shown in FIG. 4B, every scribe line 402 has an instance of the prescribed pattern 404 at the same location relative to edges of each die 302. The locations of the prescribed pattern in a small subset (e.g., five or six) of the dies 302 are added to the defect map and subsequently used by the processor 106 of SEM 104 for the defect offset determination. In other embodiments, only a small subset of the scribe lines 402 have the prescribed pattern. The processor 102 is configured for selecting a subset of the occurrences of the pattern in a respective subset of the scribe lines for incorporation into the defect map.

Figure 5:
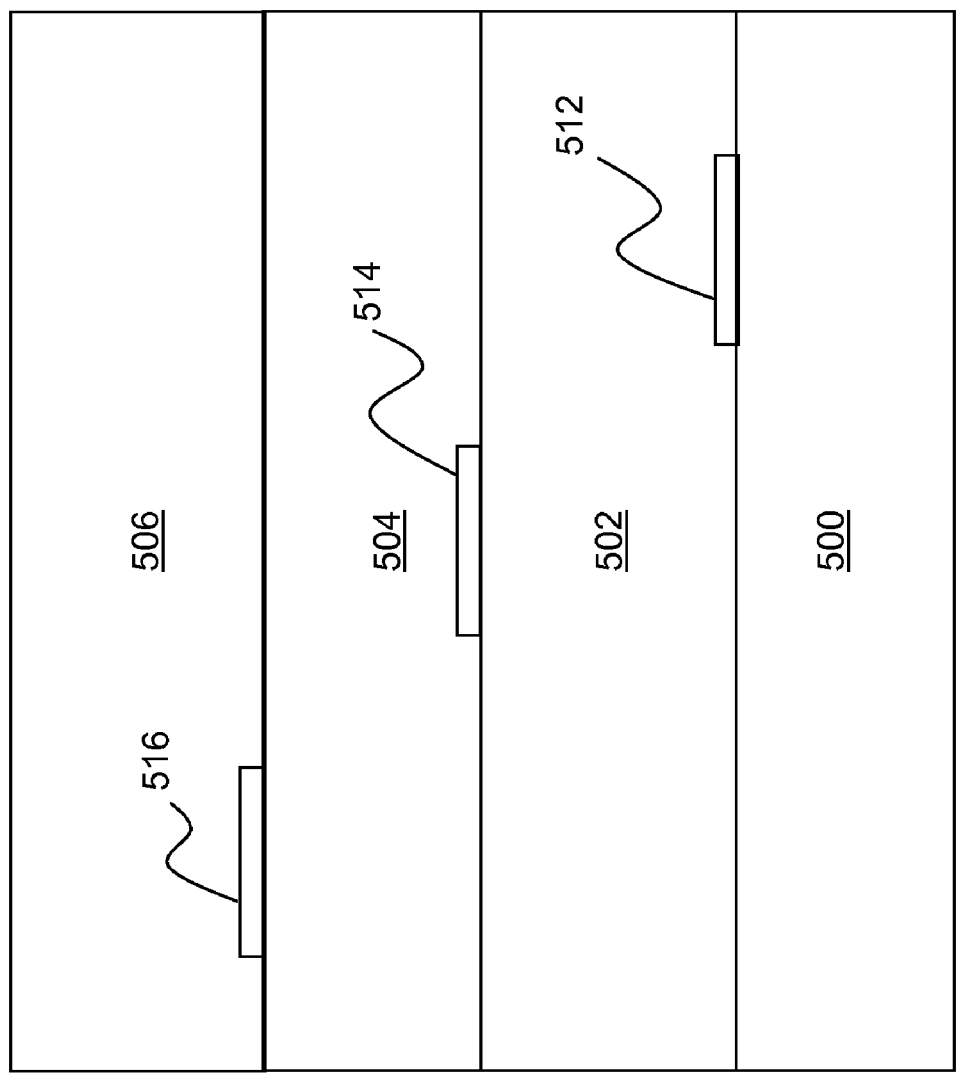
FIG. 5 is a cross sectional diagram showing some of the possible locations for the prescribed pattern in FIGS. 3 and 4, in accordance with an embodiment.

FIG. 5 is a cross sectional diagram showing some of the possible locations for the prescribed pattern. The wafer 500 includes the semiconductor substrate 500, having one or more inter-metal dielectric (IMD) layers 502 formed over the substrate 500. For example, an IMD layer 502 may be formed on substrate 500. One or more optically transparent layers 504 are formed over the substrate. For example, optically transparent layer 504 may be formed on IMD layer 502. Ono or more photoresist layers 506 are formed over the substrate. For example, photoresist layers 506 may be formed on optically transparent layers 504. This configuration is only one example, and any sequence of layers of any materials may be formed on the substrate.

In some embodiments, the prescribed pattern 512 is formed under or within an inter-metal dielectric layer 502.

In some embodiments, the prescribed pattern 514 is formed under or within an optically transparent layer 504.

In some embodiments, the prescribed pattern 516 is formed under or within a photoresist layer 506.

This is only one example; the prescribed pattern may be formed in any layer.

Portions of the apparatus described above may be embodied in the form of computer-implemented processes and apparatus for practicing those processes. These elements may also be embodied in the form of computer program code embodied in tangible machine readable storage media, such as random access memory (RAM), floppy diskettes, read only memories (ROMs), CD-ROMs, DVD-ROMs, BD-ROMs, hard disk drives, flash memories, or any other machine-readable storage medium, wherein, when the computer program code is loaded into and executed by a computer, the computer becomes an apparatus for practicing the invention. These elements may also be embodied in the form of computer program code stored in a tangible storage medium, loaded into and/or executed by a computer, such that, when the computer program code is loaded into and executed by a computer, the computer becomes an apparatus for practicing the invention. When implemented on a general-purpose processor, the computer program code segments configure the processor to create specific logic circuits. Elements of the embodiments may alternatively be embodied in a digital signal processor formed of application specific integrated circuits for performing a method according to the principles of the invention.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:
1. A method comprising:
using a semiconductor processing tool to form a prescribed pattern at a plurality of known locations on a semiconductor wafer;
incorporating the plurality of known locations into a defect map that is stored in a non-transitory, machine readable storage medium, wherein the defect map includes a location of at least one defect detected by an in-line inspection of the wafer;

transmitting the defect map including the plurality of known locations and the location of the at least one defect from a processor coupled to the tool to a scanning electron microscope (SEM), wherein the SEM has a processor that uses the known locations to calculate a defect offset for use in imaging the at least one defect in the SEM.

2. The method of claim 1, wherein the wafer has a plurality of scribe lines, and the known locations are located in at least two of the scribe lines.

3. The method of claim 2, wherein the prescribed pattern is different from any pattern formed in a product die on the wafer.

4. The method of claim 1, wherein the wafer has a plurality of scribe lines, and an occurrence of the prescribed pattern is formed in each of the scribe lines at respective known locations, the method further comprising:

selecting a subset of the occurrences of the prescribed pattern in a respective subset of the scribe lines for incorporation into the defect map.

5. The method of claim 1, wherein the wafer has a plurality of dies, and the known locations are located in at least two of the dies.

6. The method of claim 1, wherein the wafer has a plurality of dies, and an occurrence of the prescribed pattern is formed in each of the dies at respective known locations, the method further comprising:

selecting a subset of the occurrences of the prescribed pattern in a respective subset of the dies for incorporation into the defect map.

7. The method of claim 1, wherein the prescribed pattern is formed under or within an optically transparent layer.

8. The method of claim 1, wherein the prescribed pattern is formed under or within a photoresist layer.

9. The method of claim 1, wherein the prescribed pattern is formed under or within an inter-metal dielectric layer.

10. The method of claim 1, further comprising using the known locations to calculate a defect offset within the process, and imaging the at least one defect in the SEM.

11. Apparatus comprising:
a semiconductor processing tool for forming a prescribed pattern at a plurality of known locations on a semiconductor wafer;
a processor for incorporating the plurality of known locations into a defect map that includes a location of at least one defect detected by an in-line inspection of the wafer in the tool,
the processor configured for transmitting the defect map including the plurality of known locations and the location of the at least one defect to a scanning electron microscope (SEM),
wherein the SEM has a processor configured to use the known locations to calculate a defect offset for use in imaging the at least one defect in the SEM.

12. The apparatus of claim 11, wherein the wafer has a plurality of scribe lines, and an occurrence of the pattern is formed in each of the scribe lines at respective known locations, wherein:

the processor is configured for selecting a subset of the occurrences of the pattern in a respective subset of the scribe lines for incorporation into the defect map.

13. The apparatus of claim 11, wherein the wafer has a plurality of dies, and an occurrence of the pattern is formed in each of the dies at respective known locations, wherein:

the processor is configured for selecting a subset of the occurrences of the pattern in a respective subset of the dies for incorporation into the defect map.

14. A non-transitory machine readable memory or storage medium comprising computer instructions stored therein for causing a processor to perform:

controlling a tool to form a prescribed pattern at a plurality of known locations on a semiconductor wafer;

incorporating the plurality of known locations into a defect map that includes a location of at least one defect detected by an in-line inspection of a wafer;

transmitting the defect map including the plurality of known locations and the location of the at least one defect to a scanning electron microscope (SEM), wherein the SEM has a processor that uses the known locations to calculate a defect offset for use in imaging the at least one defect in the SEM.

15. The non-transitory machine readable memory or storage medium of claim 14, wherein the wafer has a plurality of scribe lines, and the controlling step includes causing the tool to form the prescribed pattern in at least two of the scribe lines.

16. The non-transitory machine readable memory or storage medium of claim 14, wherein the wafer has a plurality of scribe lines, and an occurrence of the prescribed pattern is formed in each of the scribe lines at respective known locations, the memory or medium further comprising computer instructions stored therein for causing the processor to perform:

selecting a subset of the occurrences of the prescribed pattern in a respective subset of the scribe lines for incorporation into the defect map.

17. The non-transitory machine readable memory or storage medium of claim 14, wherein the wafer has a plurality of dies, and an occurrence of the prescribed pattern is formed in each of the dies at respective known locations, the memory or medium further comprising computer instructions stored therein for causing the processor to perform:

selecting a subset of the occurrences of the prescribed pattern in a respective subset of the dies for incorporation into the defect map.

18. The non-transitory machine readable memory or storage medium of claim 14, wherein the prescribed pattern is formed under or within an optically transparent layer.

19. The non-transitory machine readable memory or storage medium of claim 14, wherein the prescribed pattern is formed under or within a photoresist layer.

20. The non-transitory machine readable memory or storage medium of claim 14, wherein the prescribed pattern is formed under or within an inter-metal dielectric layer.

* * * * *